United States Patent
Ghesu et al.

(10) Patent No.: US 10,032,281 B1
(45) Date of Patent: Jul. 24, 2018

(54) MULTI-SCALE DEEP REINFORCEMENT MACHINE LEARNING FOR N-DIMENSIONAL SEGMENTATION IN MEDICAL IMAGING

(71) Applicant: Siemens Healthcare GmbH, Erlangen (DE)

(72) Inventors: Florin Cristian Ghesu, Erlangen (DE); Bogdan Georgescu, Plainsboro, NJ (US); Dorin Comaniciu, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/661,675

(22) Filed: Jul. 27, 2017

Related U.S. Application Data

(60) Provisional application No. 62/500,604, filed on May 3, 2017.

(51) Int. Cl.
| | | |
|---|---|---|
| *G06K 9/00* | (2006.01) | |
| *G06T 7/12* | (2017.01) | |
| *G06N 3/08* | (2006.01) | |
| *G06N 3/04* | (2006.01) | |
| *G06F 19/00* | (2018.01) | |
| *G06T 7/13* | (2017.01) | |

(52) U.S. Cl.
CPC .............. *G06T 7/12* (2017.01); *G06F 19/321* (2013.01); *G06N 3/0472* (2013.01); *G06N 3/08* (2013.01); *G06T 7/13* (2017.01); *G06T 2207/10028* (2013.01); *G06T 2207/20081* (2013.01); *G06T 2207/30004* (2013.01)

(58) Field of Classification Search
CPC ............. G06T 2207/10028; G06T 7/12; G06T 2207/20081
See application file for complete search history.

(56) References Cited

U.S. PATENT DOCUMENTS

| | | | |
|---|---|---|---|
| 2012/0230572 A1* | 9/2012 | Kohlberger | G06K 9/6209 382/131 |
| 2015/0235360 A1* | 8/2015 | Zheng | G06K 9/46 382/128 |
| 2017/0071562 A1* | 3/2017 | Suzuki | A61B 6/5205 |
| 2017/0071671 A1 | 3/2017 | Neumann et al. | |
| 2017/0091574 A1* | 3/2017 | Udupa | G06K 9/4638 |
| 2017/0109881 A1* | 4/2017 | Avendi | G06T 7/0012 |

(Continued)

OTHER PUBLICATIONS

Tu, Zhuowen, and Song-Chun Zhu. "Image segmentation by data-driven Markov chain Monte Carlo." IEEE Transactions on pattern analysis and machine intelligence 24.5 (2002): 657-673.

(Continued)

*Primary Examiner* — Oneal R Mistry

(57) ABSTRACT

Multi-scale deep reinforcement learning generates a multi-scale deep reinforcement model for multi-dimensional (e.g., 3D) segmentation of an object. In this context, segmentation is formulated as learning an image-driven policy for shape evolution that converges to the object boundary. The segmentation is treated as a reinforcement learning problem, and scale-space theory is used to enable robust and efficient multi-scale shape estimation. By learning an iterative strategy to find the segmentation, the learning challenges of end-to-end regression systems may be addressed.

20 Claims, 2 Drawing Sheets

(56) References Cited

U.S. PATENT DOCUMENTS

2017/0116497 A1    4/2017  Georgescu et al.
2017/0258526 A1*   9/2017  Lang ..................... A61B 34/10
2018/0033144 A1*   2/2018  Risman ................ G06T 7/0014

OTHER PUBLICATIONS

Chan, et al.; Active Contours Without Edges; In IEEE Transactions on Image Processing, vol. 10, No. 2, Feb. 2001 (pp. 266-277).
Ghesu, et al; "Marginal Space Deep Learning: Efficient Architecture for Volumetric Image Parsing". IEEE Transactions on Medical Imaging, vol. 35, No. 5, May 2016.
Long, Jonathan, Evan Shelhamer, and Trevor Darrell. "Fully convolutional networks for semantic segmentation." Proceedings of the IEEE Conference on Computer Vision and Pattern Recognition. 2015.
Salimans, Tim, et al. "Evolution strategies as a scalable alternative to reinforcement learning." arXiv preprint arXiv:1703.03864 (2017).

* cited by examiner

MULTI-SCALE DEEP REINFORCEMENT MACHINE LEARNING FOR N-DIMENSIONAL SEGMENTATION IN MEDICAL IMAGING

RELATED APPLICATIONS

The present patent document claims the benefit of the filing date under 35 U.S.C. § 119(e) of Provisional U.S. Patent Application Ser. No. 62/500,604, filed May 3, 2017, which is hereby incorporated by reference.

BACKGROUND

The present embodiments relate to segmentation in medical imaging. Accurate and fast segmentation of anatomical structures is a fundamental task in medical image analysis, enabling real-time guidance, quantification, and processing for diagnostic and interventional procedures. Previous solutions for three-dimensional segmentation are based on machine learning driven active-shape models, front-propagation theory, Markov random field methods, or deep image-to-image regression models.

Active-shape models and front-propagation theory solutions propose parametric surface models, which are deformed to fit the boundary of the target object. Machine learning techniques leverage image databases to learn complex parametric models. The deformation is either driven by pre-trained boundary classifiers or implicitly described as a level-set. These methods may suffer from several limitations, such as suboptimal local convergence and limited scalability. For high-resolution volumetric data, the use of scanning paradigms for boundary fitting lead to significant computational challenges.

In contrast, the Markov random field methods and deep image-to-image regression models include solutions that either formulate the segmentation task as the minimization of a voxel-based energy model or an end-to-end regression process from input volume to the segmentation mask. In practice, the minimization of the underlying objective functions is tedious with the search often converging to suboptimal local solutions. The same effect can be observed when applying local boundary classifiers, which are missing essential global context.

SUMMARY

By way of introduction, the preferred embodiments described below include methods, systems, instructions, and computer readable media for N-dimensional (e.g., 3D) segmentation based on machine learning. In a medical imaging system, multi-scale deep reinforcement learning is used for segmentation. The machine-learnt model includes a policy for actions on how to segment. Iterative refinements evolve the shape according to the policy, eventually identifying boundaries of the object being segmented. The evolution includes scale, using context in the medical scan data at different resolutions in different iterations for evolving the shape. Various shape descriptors provide the evolution or refinement context, such as a statistical shape model, front propagation model, or a voxel mask model.

In a first aspect, a method is provided for three-dimensional segmentation based on machine learning in a medical imaging system. A medical dataset representing a three-dimensional region of a patient is loaded from memory. A machine applies the medical dataset to a multi-scale deep reinforcement machine-learnt model. The multi-scale deep reinforcement machine-learned model was trained with multi-scale deep reinforcement learning to segment boundaries of a three-dimensional object from the medical dataset. The multi-scale deep reinforcement machine-learnt model includes a machine-learnt policy for shape evolution over iterative refinements of the boundaries. The boundaries and refinements are described using statistical shape-modeling, front propagation modeling, or voxel mask modeling. A renderer renders an image of the three-dimensional object based on the boundaries determined with the policy.

In a second aspect, a method is provided for multi-dimensional segmentation based on machine learning in a medical imaging system. A medical dataset representing a multi-dimensional region of a patient is loaded from memory. A machine applies the medical dataset to a multi-scale, deep reinforcement machine-learnt model. The multi-scale, deep reinforcement machine-learned model was trained with multi-scale, deep reinforcement learning to segment boundaries of a multi-dimensional object from the medical dataset. The multi-scale, deep reinforcement machine-learnt model includes a machine-learnt policy for shape evolution over iterative refinements of the boundaries in scale and location. A graphics processor generates an image of the multi-dimensional object based on the boundaries determined with the policy.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Multi-scale deep reinforcement learning generates a multi-scale deep reinforcement model for N-dimensional (e.g., 3D) segmentation of an object where N is an integer greater than 1. In this context, segmentation is formulated as learning an image-driven policy for shape evolution that converges to the object boundary. The segmentation is treated as a reinforcement learning problem, and scale-space theory is used to enable robust and efficient multi-scale shape estimation. By learning an iterative strategy to find the segmentation, the learning challenges of end-to-end regression systems may be addressed.

Despite being trained as a complete segmentation method, the trained policy may instead or also be used for shape-refinement as a post-processing step. Any segmentation approach provides an initial segmentation. The machine-learnt policy is used to refine the segmentation given the original segmentation as an initial segmentation in the multi-scale deep reinforcement machine-learnt model.

Machine learning results in a machine-learnt model with a trained artificial agent. For training, many (e.g., hundreds or thousands) samples with known ground truth (e.g., segmented results) are used. The model is trained to segment a particular object or groups of objects. Different models are trained to segment different objects. Alternatively, one model is trained to segment multiple objects. Once trained, data for a particular patient is applied to the model. The model outputs the segmentation of the object or objects for that patient.

The object is three-dimensional, but may be two, four or other number of dimensions. The object and scan data are N or multi-dimensional where N is an integer greater than 1. A patient is scanned using computed tomography (CT), magnetic resonance (MR), ultrasound, C-arm x-ray, positron emission tomography (PET), single photon emission computed tomography (SPECT), or other imaging modality, resulting in data representing the patient in N dimensions. The spatial distribution of measurements is along two or more (e.g., N) spatial dimensions. 3D spatial distribution provides a medical dataset for the patient in a uniform or non-uniform grid (e.g., M×O×P, where each of M, O, and P are an integer greater than 1). The medical dataset is formed from voxels with each voxel having a scalar value for the measurement. The object is represented by multiple voxels within the scan volume. The segmentation identifies the boundaries of the object and/or all the voxels representing the object. For 2D, the object is represented by pixels. An N dimensional object includes boundaries, such as curves or surfaces, that may be different for different patients. 3D scan data and object are used for examples below, but any N dimensional object and/or scan data may be used. The object has the same or lower dimensionality as the scan data.

Figure 1:
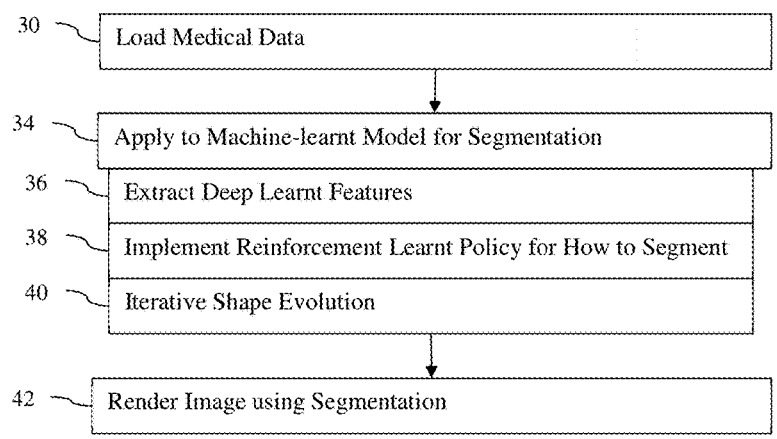
FIG. 1 is a flow chart diagram of an embodiment of a method for three-dimensional segmentation based on a multi-scale deep reinforcement machine-learnt model in a medical imaging system.

FIG. 1 shows one embodiment of a method for multi-dimensional segmentation based on machine learning in a medical imaging system. The machine-learnt model or artificial intelligence agent is applied. For a given patient, the 3D object of interest is to be segmented. The artificial intelligence agent is applied to the scan dataset with or without other input information, outputting voxels or indicating locations of the 3D object. The boundaries of the object as represented in the medical dataset are found by iteratively evolving a shape of the object using the learned policy and a shape descriptor.

Figure 3:
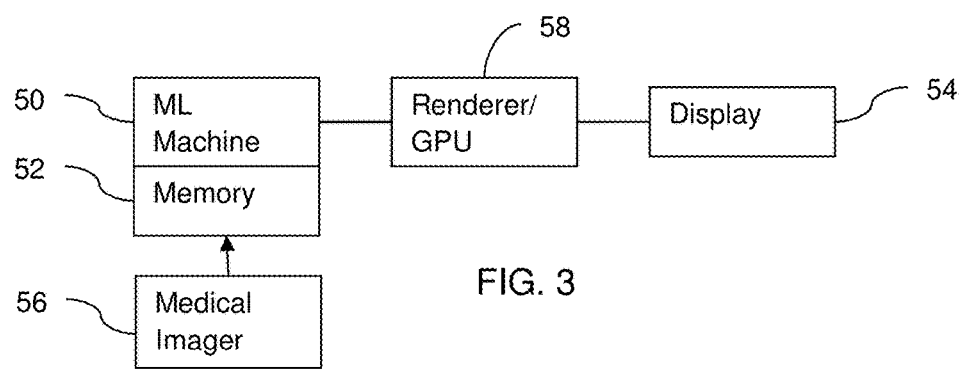
FIG. 3 is a block diagram of one embodiment of a system for learning and/or applying a multi-scale, deep reinforcement machine-learnt model.

The method is implemented by the system of FIG. 3 or another system. For example, the method is implemented by a computer, server, or other processor, a graphics processing unit or other renderer, and a display. Medical data is loaded from memory. A computer applies the machine-learnt model, outputting the segmentation. A renderer renders an image from the medical data using the segmentation. The image indicates the segmented object, such as being just of the object or highlighting the object. Different devices may be used, such as a controller or medical scanner processor performing the application and/or rendering.

Additional, different, or fewer acts may be provided. For example, the rendering of act 42 is not provided, but instead the segmentation is stored or transmitted for later rendering or for calculation of characteristics of the object. In another example, an act for scanning the patient to provide the medical dataset instead or in addition to the loading of medical data in act 30 is provided.

The acts are performed in the order shown (e.g., top to bottom or numerical) or other orders. For example, acts 36-40 represent components of the application of act 34, so are performed in any order or simultaneously as part of the application of the machine-learnt model.

In act 30, medical data is loaded from a memory, sensors, and/or other source. A medical scanner may provide the data, such as a medical dataset representing a 3D region of the patient. Mining of a patient's computerized medical record may be used. Medical information from a picture archiving and communications server may be obtained. Any source may be used.

The medical data is for a given patient. While the training may use samples from many patients, the learnt model is applied to the medical data for a patient to output a segmentation of an object for that patient. The same or different machine-learnt models are applied to data for any number of patients.

Any type of medical data is obtained. Scan data representing a 3D volume is loaded as a medical dataset. The scan data may be from multiple two-dimensional scans or may be formatted from a 3D scan. The medical data may include non-image or non-scan data, such as patient test results, physician notes, lab results, diagnosis information, billing codes, clinical data, patient history, or other information.

The medical dataset includes the information learned to be used by the machine-trained model. Ground truth information and/or reward information may be not provided. The context to be used to determine the locations of the object is provided to the machine-learnt model. For example, just the 3D scan data is provided as a medical dataset for a given patient. As another example, the 3D scan data and diagnostic information are provided as the medical dataset for the patient. The diagnostic information may be used to select the machine-learnt model to use and/or be part of the input feature vector.

In act 34, the medical dataset is applied to the machine-learnt model. The loaded medical dataset is processed by a machine, such as a computer, processor, or server. The machine uses the internal representation of the machine-learnt model. An input feature vector is created from and/or is the medical dataset. The machine inputs the feature vector to the machine-learnt model, resulting in the machine-learnt model outputting the segmentation.

The trained model is stored in a memory. The trained artificial intelligence (i.e., machine-learnt model) is stored. The result of the training is a matrix. The matrix represents the learned knowledge through machine training. The matrix includes an input vector and outputs for the segmentation. Other machine-learnt model representations may be used, such as a hierarchy of matrices or other non-linear models.

Any memory may be used. The memory used for the training data may be used. For application, the memory may be in other devices. For example, the trained model is stored in a memory of a server. The server uses the trained model to output segmentation to clients or to a server-based renderer which outputs rendered images to the clients. As another example, multiple copies of the trained model are provided to different physicians, medical scanners, and/or workstations for use by different physicians.

Acts 36-40 represent different aspects in applying the machine-learnt model. Additional, different, or fewer aspects may be provided. The machine-learned model was previously learned using deep learning (e.g., deep neural network), so extracts deep learnt features in act 36. The training learns filter kernels, policy, and/or other information used to segment. This training may be based on learnt information extracted from the input data. By applying the deep-learnt model in act 36, features are extracted from the medical dataset. The machine-learnt model was previously learned using reinforcement learning. A reward system is used to learn how to segment through a series of actions. The training learns a policy in act 38 indicating how to segment through a sequence of optimizations or shape evolutions of act 40. The multi-scale deep reinforcement machine-learnt model is learnt using deep reinforcement learning allowing actions at different scales (e.g., resolution or amount of zooming).

Reinforcement learning may be used to improve the experiment design. The decision support system learns the optimal or a variety of actions for segmenting rather than merely learning to classify each voxel as belonging to or not belonging to the object. Machine learning techniques are used to automatically identify the best or other options for how to segment among the available alternatives. The reinforcement learning learns a "policy" (e.g., a guideline of how to optimize the segmentation). Because different actions may be used (e.g., what shape parameters to alter in what sequence, what sequence to use given the patient data or feedback from fitting with patient data, which convolution filters to use at which state, what scale to use at each stage or state, and/or which classifier to apply), the segmentation may be encoded as a Markov decision process. An optimal policy may be computed from the Markov decision process using, for example, dynamic programming or more advanced reinforcement learning techniques such as Q-Learning. During the learning procedure, an agent repeatedly tries different actions from the set of available actions to gain experience, which is used to learn an optimal policy. A policy determines for any possible state during the decision process the best action to perform to maximize future rewards. The rewards are set up in a way such that positive rewards are given for actions that lead to fast and reliable (low uncertainty) segmentation, while negative rewards are given for experiments which provide little or no value to the decision-making process. Only positive or only negative rewards may be used. Experience from past decision-making processes may be used to define the rewards and the states, and segmentations for past patients may be used to learn the set of actions.

In one embodiment, the multi-scale deep reinforcement machine-learnt model is trained with the Markov decision process including feature extraction for the three-dimensional object and effective finite-horizon policy learning of the machine-learnt policy. Let $M=(S, A, r, \gamma)$ be a Markov decision process, where $S(I, \Omega) \in S$ defines a compact system-state with $I \in \mathbb{R}^3$ representing the image context and $\Omega$ as a pre-defined shape-representation (e.g. image voxel mask model or an explicit or implicit parametric shape model such as a statistical shape model or front propagation model). A defines the action-space with actions controlling the shape-evolution. $r: S \times A \times S \to \mathbb{R}$ denotes the reward system used as incentive to control the convergence. $\gamma \in (0,1)$ controls immediate versus future rewards. Other reinforcement learning and/or Markov decision process training may be used.

The target is to train an optimal behavior policy $\pi^*: S \times \to [0,1]^{|A|}$ for an intelligent artificial agent which strategically evolves the current shape $\Omega$ to improve the segmentation based on active image context. The pre-defined shape model evolves over application of the policy to better fit the medical dataset of the patient. Iterative refinement controlled by the learnt policy optimizes the segmentation.

The policy defines the actions to take given a current fit or current shape relative to the image context (i.e., relative to the medical dataset) to improve the segmentation. The actions may include change of scale using scale-space. The initial and/or final scale may be learnt or manually restricted, such as requiring the initial segmentation to be at a coarse scale and the final segmentation to be at the finest or highest resolution scale of the medical dataset. Any reward may be used for training, such as a measure of difference from ground truth or Dice coefficient. In the reinforcement training, the intelligent agent learns which actions (e.g., which shape parameters to change and by how much) given the current shape and image context based on the reward. The resulting change or action is rewarded or not, so the training determines the actions for a given situation that provide the greatest reward and/or minimize penalty. The path of action to find the boundary or object, including changes in scale, is learnt. For application, this learnt policy is applied without measuring reward.

For training, the training data includes many samples. The samples are medical datasets with known segmentation as the ground truth. In alternative or additional embodiments, the samples include actions taken to segment as the ground truth. The deep learning learns features to be extracted from the medical dataset. These learnt features are to be used by the learnt policy. The features that may be used to best or sufficiently distinguish between actions are learned from the training data. For example, deep learning (e.g., deep structured learning, hierarchical learning, or deep machine learning) models high-level abstractions in data by using multiple processing layers with structures composed of multiple non-linear transformations, where the input data features are not engineered explicitly. A deep neural network processes the input via multiple layers of feature extraction to produce features used to segment. The deep learning provides the features used to segment. Other deep learnt, sparse auto-encoding models may be trained and applied. The machine training is unsupervised in learning the features to use and how to classify given an input sample (i.e., feature vector).

For training, deep Q-learning combines the advantages of automatic image-feature extraction with effective finite-horizon policy learning. The action space may be proportional to the image space, so there are many options from which to learn the optimal policy. Q-learning may be less effective with hundreds, or more optional actions for refinement or evolution. In one alternative, action embedding in combination with policy gradient is used to exploit the intrinsically sparse structure of the relevant action space. In another embodiment, natural evolution strategies (NES) performs the policy exploration in parameter space as part of the learning. NES is particularly suited given the compact parametrization of fully-convolutional networks. Other approaches for deep reinforcement learning may be used.

The training provides a multi-scale deep reinforcement machine-learnt model. This model is trained to segment boundaries of a 3D object from the medical dataset. The medical dataset is input, and the model outputs the boundaries. The boundaries extend over different dimensions to any extent. The boundaries are identified by voxel, by shape, or other representation. The boundaries are for just the exterior or may also include the interior of the object.

In act 34, the machine applies the medical dataset to the multi-scale deep reinforcement machine-learnt model. The learnt model, using a shape descriptor, defines an action space. The learnt policy of the model provides an action or actions for each iteration of shape evolution. The action changes some aspect of the shape descriptor, refining the location and/or scale for the shape descriptor. Different shapes of the 3D object result from different iterations of shape evolution controlled by the learnt policy. The scale and/or locations of the current estimate of the object are changed for each iteration to find a best segmentation. For each iteration, the locations of the 3D object are estimated based on an action corresponding to a change in one or more values of parameters of the shape descriptor. The machine-learnt policy controls the shape evolution over the iterative refinements of the boundaries given the image context. The policy provides decision making for creating a sequence of acts in how to segment given the feedback of the medical dataset context for a particular patient. This evolves the shape specific to the patient based on the learned process or actions optimized to segment over a wide population of patients.

The training and application disclosed in U.S. Published Patent Application No. 2017/0116497, the disclosure of which is incorporated herein by reference, may be used for segmentation rather than landmark detection. The multi-scale iteration scheme ensures robustness and optimal convergence speed for the segmentation. By using actions across coarse and fine dataset context, false positives may be avoided. The segmentation is of a 3D object, so the parameter space is different as compared to landmark detection. The parameter space defined by the shape descriptor is different than used for landmark detection.

For object segmentation, the parameter space is based on statistical shape-modeling, front propagation modeling, or voxel mask modeling. Other parameterization models may be used. These models define a shape of the object in three dimensions. The boundaries of the object in each iteration are indicated by the values of the parameters defining the shape. The refinements indicated by the learnt policy are actions in the parameter space of these models, such as the action being a change in one or more values of a parameter of the shape-descriptor model. The multi-scale deep reinforcement machine-learnt model trained with the Markov decision process includes a compact system-state of the medical dataset and a shape representation. The shape representation is a shape descriptor given by the statistical shape-modeling, the front propagation modeling, or the voxel mask modeling.

Figure 2:
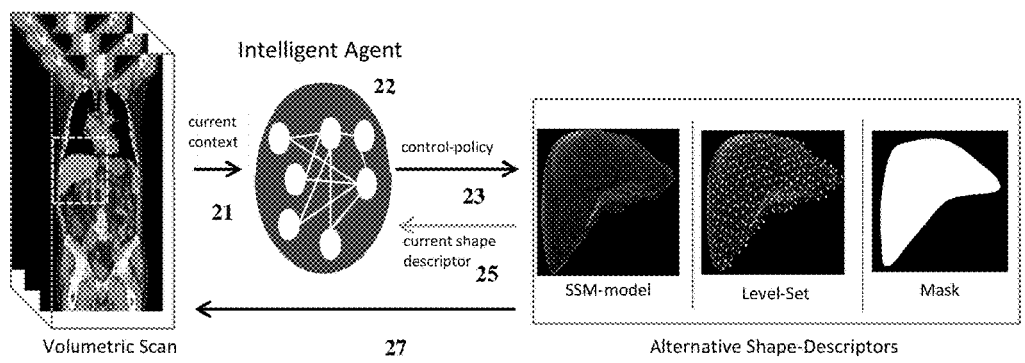
FIG. 2 illustrates iterative refinement in a multi-scale, deep reinforcement machine-learnt model.

FIG. 2 illustrates the iterative segmentation using the machine-learnt model. Three alternative shape representation models 24 are shown, statistical shape model (SSM), level-set (front propagation model), and voxel mask model. One of these or another shape representation model 24 is used for training and application. The shape representation model 24 describes the underlying shape fit to the object in the medical dataset 20. The medical dataset 20 from a volumetric scan (e.g., 3D CT scan) provides the patient-specific context for the segmentation of an object (e.g., liver shown in region of interest box). The intelligent agent 22 is the multi-scale deep reinforcement machine-learnt model, including the learnt policy in an action space defined by the shape descriptor model 24.

In an initial iteration, the intelligent agent 22 receives the medical dataset 20 as the current context 21. The intelligent agent 22 extracts values for deep learnt features and outputs a new or initial value for one or more parameters of the shape descriptor model 24 based on the values for the features. The control-policy learnt shape-evolution 23 is an action in the form of a change in the shape. The shape model of the shape descriptor model 24 is altered based on the action from the policy. The resulting shape descriptor 25 is provided to the intelligent agent 22. For a next iteration, the context 21 and the corresponding current shape 25 are used by the intelligent agent 22 to determine a next refinement or shape evolution 23. In each iteration, the machine-learnt policy controls the shape descriptor model 24 to provide a next shape descriptor 25. The current shape 27 may be fed back to or used to access contextual information from the medical dataset 20. The sampling of context information may depend, at least in part, on the current mesh or shape (e.g., extracting scalar voxel values based on normal, tangent, and/or neighborhood of the current fit shape). The intelligent agent 22 may control or select the scale of the context, such as by down sampling for coarse scale.

The iterations continue until a stop criterion or criteria are met. Any stop criterion may be used. For example, the refinements stop where the same refinements are repeated or pairs of refinements cycle the shape descriptor 25 between two similar states. Other criteria may include a number of iterations, a measure of distance of the shape descriptor 25 from the medical dataset 20, or a chi-square value. An explicit 'stop' action may be used.

Any shape-descriptor model 24 may be used within the framework of FIG. 2. Different shape-descriptor models 24 may capture different aspects of the object. This allows the exploitation of the shape-properties of the underlying structure (e.g., size and surface variation and/or local rigidity) to reach optimal segmentation performance. The choice of shape descriptor model 24 has a direct effect on the definition of the state and action spaces, as well as the underlying reward-system.

In one embodiment, the shape-descriptor model 24 is a statistical shape model (SSM). For example, an SSM for the liver is learnt from ground truth segmentations for the liver, an atlas, or another source. The SSM is from the same or different training data used to create the multi-scale deep reinforcement machine-learnt model. Given explicit point correspondences among different parametrized shapes $x \in \mathbb{R}^M$, the shape is encoded, such as using a linear model for shape variation. This encoding of the shape fit to the context defines the boundaries of the object. While typically a dense point cloud is used for a precise delineation, principal component analysis may be used to project the shape to a compact space, spanned by the main modes of deformation: $e = \Phi(x - \bar{x})$, where $e \in \mathbb{R}^T$, $T \ll M$. Other explicit parametrizations may be used.

The boundaries and the refinements are described using the SSM. The modes of deformation define the actions that may be taken. In this context, the shape is evolved by varying the T shape-modes (either individually or jointly). The change or action output by the policy for shape evolution is a change in one or more of the shape parameters of the projected shape space of the SSM. In this case, the state is parametrized by the current shape, for example by extracting image context at the shape boundary and aggregating that information to learn the optimal policy for changing individual shape-parameters in the projected shape-space. This solution may be effectively applied multi-scale and does not have the same memory requirements as image-to-image solutions. Typically, the image is sampled using different orientations around the boundary, which is a potentially tedious and slow process. Spectral shape decomposition may be used to encode the shape.

The reward-system may be a point-to-point distance function (e.g., minimum sum of absolute differences). Any segmentation quality metric may be used, such as the Dice coefficient.

In another embodiment, the shape descriptor model 24 is a front propagation model. Any front propagation may be used, such as a level-set. The implicit shape representation, such as a level-set, is represented as $\phi: \mathbb{R}^N \rightarrow \mathbb{R}$. In an Eulerian formulation, the motion of this hypersurface is modeled using a speed function F, which may depend on normal surface direction, local curvature, or other geometric measurement. For example, the contour function is given as $\phi_t + F|\nabla\phi| = 0$. The boundaries are described using this level-set. Other implicit parameterizations may be used.

The refinement in the action space changes a value of one or more parameters of this front propagation model. The level-set is altered to evolve the shape for segmentation. By examining the gradients at normal to the contour in the image context, the segmentation evolves. The initial level set may be required to be within the object so that the contour shifts to the boundaries. The optimal policy controls the speed of the particles given by the speed function using robust image-features. The change in the speed of the particles in the hypersurface of the front propagation model defines the action. By considering a multi-scale shape evolution, limitations of level-set methods may be addressed, such as sensitivity to noise and robustness under partial shape-occlusion. For example, the shape is started close so that the actions in the evolution are simpler. By using a coarse segmentation initially, the closeness for finer resolutions is provided.

Any metric used for shape-evolution or segmentation methods may be used. For example, the Dice coefficient, Jaccard index, a correlation, or a distance function is used.

In another alternative embodiment, the shape descriptor 24 is a voxel mask model. The segmentation may be directly labeled as a mask. The state-space S is defined by the set of pairs of static image context. The pairs use the multi-scale, providing global or local volumetric patches. The state of each voxel defines the corresponding segmentation mask, providing the boundaries of the object in three dimensions.

The refinement is described by state change. The actions are for change of state. For example, a given segmentation mask in a particular state is updated voxel-wise using one of three discrete actions: flip-labeled to unlabeled, flip-unlabeled to labeled, keep the current label. The action may be for any sampling of voxels based on the selected scale. The action may also be for which voxels to change. Rather than evolving voxel by voxel, action schemes using correlation with adjacent voxels may be used. Groups of voxels are switched or not switched. The size of the grouping (e.g., multi-scale) may be another action. This correlated voxel-labeling may ensure the effective exploration of the state-space. Using this definition, the task is to learn an optimal decision policy that iteratively generates a mask converging to the true segmentation of the target anatomical structure. The evolution changes the state of one or more voxels. The evolution of the voxel mask provides for optimization compared to one-shot voxel labeling where each voxel is labeled without actions.

The reward system may be defined using the Dice coefficient. The overlap of the shape descriptor with the ground truth is determined in training. If overlapping, a reward is given. Otherwise, no reward is given. The overlap may be measured per voxel or for all voxels. Other reward functions may be used, such as chi-square or other measures of amount of difference.

In act 42 of FIG. 1, a render renders an image of the 3D object based on the boundaries determined with the policy. The image is transmitted to a display device. The locations as a binary mask or the scalar values of the medical dataset at the locations of the segmented object are used to render the 3D object to a 2D display. Surface, projection, path tracing, ray tracing, or other 3D rendering may be used. The resulting image represents the segmented object. In other embodiments, the volume represented by the medical dataset is rendered to a 2D image. For 2D, a graphics processor generates the image. The scalar values and/or locations of the segmented object are highlighted, such as providing tinting, increased brightness, or other alteration. The segmented boundaries are highlighted relative to other objects. In yet another embodiment, a 2D image is extracted as a planar slice through the volume, with the object highlighted based on the segmentation.

The segmentation may be used for additional or alternative purposes. For example, a volume, area, length, or other characteristic of the object is determined from the segmentation. Further scanning or surgical planning may use the segmentation information.

FIG. 3 shows a block diagram of one embodiment of a system for segmentation of a 3D object with a multi-scale deep reinforcement machine-learnt model. The system is for application of the machine-learnt model, but may alternatively or additionally be used for training with machine learning. Using deep learning, features determinative of actions to take and/or locations of the object are learnt. Using reinforcement learning, a policy for actions to iteratively evolve a shape descriptor is learnt. Using a scale-space, the action space includes different resolutions or scales, allowing for evolution of the shape using different scales. The shape descriptor model defines the spatial extent of the segmentation, the actions in addition to scale that may be taken to evolve the segmentation, and the rewards used for reinforcement learning. The resulting multi-scale deep reinforcement machine-learnt model segments one or more 3D objects from a medical dataset or scan data for a patient.

The system implements the method of FIG. 1 and/or the arrangement of FIG. 2. Other methods or acts may be implemented, such as acts for selecting the medical data set to process, activating application of the machine-learnt model, and/or using the segmentation (e.g., for calculating a characteristic of the segmented object).

The system includes a machine 50, a memory 52, a display 54, a medical imager 56, and a renderer 58. Additional, different, or fewer components may be provided. For example, the medical imager 56 and/or memory 52 are not provided. In another example, a network or network connection is provided, such as for networking with a medical imaging network or data archival system. A user interface (e.g., user input device) may be provided for interacting with the machine 50, renderer 58, or other components. In yet another example, the renderer 58 is a graphics processor, such as a graphics processing unit for generating a 2D image from 2D segmentation and/or scan data.

The machine 50, memory 52, renderer 58, and/or display 54 are part of the medical imager 56. Alternatively, the machine 50, memory 52, renderer 58, and/or display 54 are part of a server, workstation, or computer separate from the medical imager 56. The machine 50, memory 52, renderer 58, and/or display 54 are a personal computer, such as desktop or laptop, a workstation, a server, a network, or combinations thereof. In yet other embodiments, the machine 50 and memory 52 are part of a separate computer from the renderer 58.

The medical imager 56 is a medical diagnostic imaging system. Ultrasound, CT, x-ray, fluoroscopy, positron emission tomography (PET), single photon emission computed tomography (SPECT), MR, and/or other medical imaging systems may be used. The medical imager 56 may include a transmitter and includes a detector for scanning or receiving data representative of the interior of the patient. The medical imager 56 acquires scan data representing the patient. The scan data represents a volume of the patient (e.g., voxels distributed over all three spatial dimensions). The scan data is acquired and used for diagnosis or surgical planning.

In alternative embodiments, the medical imager 56 is not provided, but a previously acquired dataset for a patient is stored in the memory 52. In yet other alternatives, many medical images 56 are provided in the memory 52 as the training data, which is gathered and stored in the memory 52.

The scan data (e.g., medical dataset) represents all or part of an object of interest, such as an organ, implant, medical tool, tissue, bone, physiological system, or other part of the patient. The object of interest is distributed in three dimensions, so is a 3D object. Rather than detecting a point, the segmentation determines the 3D extent of the object. For example, voxels spatially distributed along each of three spatial dimensions belonging to the object are identified as segmentation.

The machine 50 is a hardware device, such as a computer, workstation, server, processor, or other device configured to apply machine learning and/or to apply a machine-learnt model. The machine 50 is configured by software, hardware, and/or firmware. For learning, the machine 50 is configured by one or more machine learning algorithms. For applying a learnt model, the machine 50 is configured, in part, by a learnt matrix or matrices associating input data to output segmentation.

The machine 50 applies a machine-learnt model, such as one learnt with deep learning. The machine-learnt model, as implemented by the machine 50, generates input features and/or locations of a 3D object based on application of medical data from a scan of a patient. By input of the scan data, the machine-learnt model follows a machine-learnt policy for actions to take for evolving a fit of a shape model to the data of a particular patient. The result of the shape evolution is identification of the locations of the 3D object as represented in the scan data (i.e., segmentation for that patient).

The memory 52 is a graphics processing memory, a video random access memory, a random access memory, system memory, cache memory, hard drive, optical media, magnetic media, flash drive, buffer, database, combinations thereof, or other now known or later developed memory device for storing training data (e.g., scan data with known segmentation of the object), medical datasets, shape descriptors, segmented results, a rendered image, information used in segmentation with the machine-learnt model, and/or other information. The memory 52 is part of the medical imager 56, part of a computer associated with the machine 50, part of a computer associated with the renderer 58, a database, part of another system, a picture archival memory, or a standalone device.

For application of the machine-learnt model, the memory 52 stores scan data representing one or more patients. For example, data from the medical imager 56 is stored. The data is in a scan format or reconstructed to a volume or three-dimensional grid format. The image context related to the evolving shape descriptor, the shape descriptor, the matrix or matrices of the machine-learnt model, values calculated as part of application, and the resulting segmentation may also be stored.

The memory 52 or other memory is alternatively or additionally a non-transitory computer readable storage medium storing data representing instructions executable by the programmed machine 50 for learning or applying the machine-learnt model. The instructions for implementing the processes, methods, and/or techniques discussed herein are provided on non-transitory computer-readable storage media or memories, such as a cache, buffer, RAM, removable media, hard drive, or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The renderer 58 is a graphics processor device, such as a graphics processing unit, graphics card, graphic chip, multi-core processor, or other hardware processor for generating an image from 3D or multi-dimensional segmentation. The renderer 58 is configured by an application programming interface to render an image from the 3D scan data representing a patient. Using physically-based, ray casting, surface rendering, path tracing, or other rendering, an image is rendered from the 3D data to a 2D screen of the display 54. The image is of the segmented object alone or with surrounding tissue or other objects.

The display 54 is a monitor, LCD, projector, plasma display, CRT, printer, or other now known or later developed device for displaying the photorealistic image or images. The display 54 receives images from the machine 50, memory 52, renderer 58, or medical imager 56. The images of the tissue captured by the medical imager 56 are displayed. The image of the segmented object is displayed. The segmented object is highlighted or displayed alone. Other information may be displayed as well, such as generated graphics, text, or quantities as a virtual overlay.

Additional images may be displayed. Where scan data represents a sequence of scans over time, a corresponding sequence of images may be generated. The segmentation for each time or image is used to represent the object over time.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for three-dimensional segmentation based on machine learning in a medical imaging system, the method comprising:

scanning, by a medical scanner, a patient, the medical scanner comprising a magnetic resonance, computed tomography, x-ray, or ultrasound imaging system;

loading, from memory, a medical dataset representing a three-dimensional region of the patient, the medical dataset being from the scanning by the medical scanner, the medical dataset comprising magnetic resonance, computed tomography, x-ray, or ultrasound data;

applying, by a machine, the medical dataset to a multi-scale deep reinforcement machine-learnt model, the multi-scale deep reinforcement machine-learned model trained with multi-scale deep reinforcement learning to segment boundaries of a three-dimensional object from the medical dataset, the multi-scale deep reinforcement machine-learnt model including a machine-learnt policy of a sequence of actions for shape evolution over iterative refinements of the boundaries of the object, the machine-learnt policy trained to select each of the actions from possibilities given a state of fitting at each of the iterative refinements, the actions including actions in different resolutions of the medical dataset, the sequence resulting from the machine-learnt policy training based on maximizing rewards, the boundaries and refinements described using statistical shape-modeling, front propagation modeling, or voxel mask modeling, the multi-scale deep reinforcement machine-learnt model trained with natural evolution strategies to explore a parameter space based on the statistical shape-modeling, front propagation modeling, or voxel mask modeling;

rendering, by a renderer, an image of the three-dimensional object based on the boundaries determined with the policy; and displaying the image on a display device.

2. The method of claim 1 further comprising loading patient information other than the medical dataset representing the three-dimensional region of the patient, and wherein applying comprises applying the medical dataset and the patient information.

3. The method of claim 1 wherein applying comprises applying with the machine-learnt policy comprising refinements of the boundaries over scale in the different resolutions and location.

4. The method of claim 1 wherein applying comprises applying with the multi-scale deep reinforcement machine-learnt model comprising an action, of the sequence of actions, in space for each of the iterative refinements and estimation of locations of the three-dimensional object based on the action for each of the iterative refinements.

5. The method of claim 1 wherein applying comprises determining different shapes of the three-dimensional object in the different iterative refinements.

6. The method of claim 1 wherein applying comprises applying to the multi-scale deep reinforcement machine-learnt model trained with deep Q-learning.

7. The method of claim 6 wherein applying comprises applying the multi-scale deep reinforcement machine-learnt model trained with the Markov decision process including a compact system-state of the medical dataset and a shape representation comprising the statistical shape-modeling, the front propagation modeling, or the voxel mask modeling.

8. The method of claim 6 wherein applying comprises applying the multi-scale deep reinforcement machine-learnt model trained with the Markov decision process including an action space controlling the shape evolution.

9. The method of claim 6 wherein applying comprises applying the multi-scale deep reinforcement machine-learnt model trained with the Markov decision process including feature extraction for the three-dimensional object and effective finite-horizon policy learning of the machine-learnt policy.

10. The method of claim 1 wherein applying comprises applying with the iterative refinements comprising interaction between an intelligent agent forming the machine-learnt policy for shape evolution and the statistical shape-modeling, front propagation modeling, or voxel mask modeling, the intelligent agent passing the shape evolution for each iteration to the statistical shape-modeling, front propagation modeling, or voxel mask modeling, and the statistical shape-modeling, front propagation modeling, or a voxel mask model passing a current shape descriptor to the intelligent agent for each iteration.

11. The method of claim 1 wherein applying comprises applying with the boundaries and refinements described using the statistical shape modeling and wherein the shape evolution comprises change in one or more shape parameters of a projected shape-space of the statistical shape modeling.

12. The method of claim 1 wherein applying comprises applying with the boundaries and refinements described using the front propagation modeling and wherein the shape evolution comprises change in a speed of particles in a hypersurface of the front propagation modeling.

13. The method of claim 1 wherein applying comprises applying with the boundaries and refinements described using the voxel mask modeling and wherein the shape evolution comprises change in state per voxel of the medical dataset of the voxel mask modeling.

14. The method of claim 1 wherein rendering the image comprises rendering from the medical dataset with the segmented boundaries highlighted.

15. A method for multi-dimensional segmentation based on machine learning in a medical imaging system, the method comprising:

scanning, by a medical scanner, a patient, the medical scanner comprising a magnetic resonance, computed tomography, x-ray, or ultrasound imaging system;

loading, from memory, a medical dataset representing a three-dimensional region of the patient, the medical dataset being from the scanning by the medical scanner, the medical dataset comprising magnetic resonance, computed tomography, x-ray, or ultrasound data;

applying, by a machine, the medical dataset to a multi-scale, deep reinforcement machine-learnt model, the multi-scale, deep reinforcement machine-learned model trained with multi-scale, deep reinforcement learning to segment boundaries of a multi-dimensional object from the medical dataset, the multi-scale, deep reinforcement machine-learnt model including a machine-learnt policy of a sequence of actions for shape evolution over iterative refinements of the boundaries in scale at different resolutions of the medical dataset and in location, the multi-scale deep reinforcement machine-learnt model trained with natural evolution strategies to explore a parameter space; and generating, by a graphics processor on a display device, an image of the multi-dimensional object based on the boundaries determined with the policy.

16. The method of claim 15 wherein applying comprises applying with the machine-learnt policy for the shape evolution uses a shape descriptor based on a level-set, statistical shape model, or voxel mask with the refinements being of a change in speed, change of a shape space parameter, or change in state, respectively.

17. The method of claim 15 wherein applying comprises applying with the shape evolution over the iterative refinements in different scales corresponding to the different resolutions.

18. The method of claim 15 wherein applying comprises applying with the shape evolution over the iterative refinements having a control output by the machine-learnt policy to a shape descriptor model and a shape descriptor output by the shape descriptor model to the machine-learnt policy based on the control.

19. The method of claim 15 wherein applying comprises applying with the multi-scale, deep reinforcement machine-learnt model trained for the sequence of actions in how to segment.

20. A method for three-dimensional segmentation based on machine learning in a medical imaging system, the method comprising:
    scanning, by a medical scanner, a patient, the medical scanner comprising a magnetic resonance, computed tomography, x-ray, or ultrasound imaging system;
    loading, from memory, a medical dataset representing a three-dimensional region of the patient, the medical dataset being from the scanning by the medical scanner, the medical dataset comprising magnetic resonance, computed tomography, x-ray, or ultrasound data;
    applying, by a machine, the medical dataset to a multi-scale deep reinforcement machine-learnt model, the multi-scale deep reinforcement machine-learned model trained with multi-scale deep reinforcement learning to segment boundaries of a three-dimensional object from the medical dataset, the multi-scale deep reinforcement machine-learnt model including a machine-learnt policy of a sequence of actions for shape evolution over iterative refinements of the boundaries of the object, including actions in different resolutions of the medical dataset, the boundaries and refinements described using front propagation modeling, or voxel mask modeling, wherein applying comprises one of:
    (a) applying with the boundaries and refinements described using the front propagation modeling and wherein the shape evolution comprises change in a speed of particles in a hypersurface of the front propagation modeling, or
    (b) applying with the boundaries and refinements described using the voxel mask modeling and wherein the shape evolution comprises change in state per voxel of the medical dataset of the voxel mask modeling;
    rendering, by a renderer, an image of the three-dimensional object based on the boundaries determined with the policy; and
    displaying the image on a display device.

* * * * *